(12) United States Patent
LeJuene et al.

(10) Patent No.: US 9,556,471 B2
(45) Date of Patent: Jan. 31, 2017

(54) ENZYME CONTAINING LIQUID AND DELIVERY SYSTEM FOR DETECTION OF ANALYTES ON SURFACES

(75) Inventors: Keith E. LeJuene, Murrysville, PA (US); Jennifer A. Bacior, Pittsburgh, PA (US); Jason A. Berberich, Lexington, KY (US); Markus Erbeldinger, Pittsburgh, PA (US); Bhalchandra Shripad Lele, Pittsburgh, PA (US)

(73) Assignee: FLIR Detection, Inc., Stillwater, OK (US)

( * ) Notice: Subject to any disclaimer, the term of this patent is extended or adjusted under 35 U.S.C. 154(b) by 1553 days.

(21) Appl. No.: 11/501,296

(22) Filed: Aug. 9, 2006

(65) Prior Publication Data
US 2010/0227345 A1    Sep. 9, 2010

(51) Int. Cl.
C12Q 1/28    (2006.01)
C12M 1/34    (2006.01)
C12Q 1/34    (2006.01)
C12Q 1/37    (2006.01)
C12Q 1/46    (2006.01)

(52) U.S. Cl.
CPC . *C12Q 1/28* (2013.01); *C12Q 1/34* (2013.01); *C12Q 1/37* (2013.01); *C12Q 1/46* (2013.01)

(58) Field of Classification Search
CPC ............... C12Q 1/28; C12Q 1/34; C12Q 1/37; C12Q 1/46; B01J 19/0046; B01J 2219/00722; B82Y 30/00; B01N 33/54366; B01N 33/54373
See application file for complete search history.

(56) References Cited

U.S. PATENT DOCUMENTS

| | | | | |
|---|---|---|---|---|
| 4,241,180 A | * | 12/1980 | Keyes et al. | 435/20 |
| 4,614,714 A | * | 9/1986 | Kusakabe et al. | 435/25 |
| 4,881,109 A | * | 11/1989 | Ogawa | 257/253 |
| 5,152,461 A | | 10/1992 | Proctor | |

(Continued)

OTHER PUBLICATIONS

Jaffrezic-Renault, N. New Trends in Biosensors for Organophosphorus Pesticides, Sensors 2001, 1, 60-74.
(Continued)

*Primary Examiner* — Michael Hobbs
(74) *Attorney, Agent, or Firm* — Buchanan Ingersoll & Rooney PC; Craig G. Cochenour, Esq.

(57) ABSTRACT

An aqueous enzyme based sensor comprising one or more enzymes and at least one indicator compound capable of indicating a reaction of at least one of the enzymes with at least one target analyte, wherein the enzyme and the indicator are capable of being delivered, preferably by being sprayed, to a surface having the target analyte without sampling the surface. An aqueous enzyme based sensor is provided that is capable of detecting an enzyme specific substrate as the analyte. This aqueous enzyme based sensor further comprises of one or more enzyme specific substrates in which the sensor detects enzyme inhibition. The aqueous enzyme based sensor optionally comprises one or more of a light scattering additive(s), an adhesive polymer(s), a protein stabilizer(s), a protein stabilizing sugar(s), a surfactant(s), and a solvent(s), and combinations thereof. A dispensing system and a method of detecting a target chemical on a surface without sampling the surface is provided.

20 Claims, 1 Drawing Sheet

(56) References Cited

U.S. PATENT DOCUMENTS

| | | | |
|---|---|---|---|
| 5,332,157 A * | 7/1994 | Proctor | 239/304 |
| 6,541,230 B1 | 4/2003 | Gordon et al. | |
| 6,750,033 B2 | 6/2004 | LeJeune et al. | |
| 6,821,738 B2 | 11/2004 | Harmon | |
| 6,846,638 B2 * | 1/2005 | Shipwash | 435/7.1 |
| 7,008,524 B2 | 3/2006 | Stanford et al. | |
| 2002/0182662 A1 * | 12/2002 | Lejeune et al. | 435/18 |
| 2004/0209339 A1 * | 10/2004 | LeJeune et al. | 435/180 |
| 2007/0029195 A1 * | 2/2007 | Li et al. | 204/403.01 |
| 2008/0193418 A1 * | 8/2008 | Walter | 424/93.6 |

OTHER PUBLICATIONS

Walker, J.P. & Asher, S.A., Acetylcholinesterase-Based Organophosphate Nerve Agent Sensing Photonic Crystal, Anal. Chem. 2005, 77, 1596-1600.

Mulchandani, A., et al., Biosensor for Direct Determination of Organophosphate Pesticides, Biosensors & Bioelectronics 16 (2001) 225-230.

Mulchandani, P. et al., Biosensor for Direct Determination of Organophosphate Nerve Agents. 1. Potentiometric Enzyme Electrode, Biosensors & Bioelectronics 14 (1999) 77-85.

Mulchandani, A. et al., Fiber-Optic Enzyme Biosensor for Direct Determination of Organophosphate Nerve Agents, Biotechnol. Prog. 1999, 15, 130-134.

Mulchandani, A. et al., Amperometric Thick-Film Strip Electrodes for Monitoring Organophosphate Nerve Agents Based on Immobilized Organophosphorus Hydrolase, Anal Chem. 1999, 71, 2246-2249.

Wang, J. et al., Remote Biosensor for In-Situ Monitoring of Organophosphate Nerve Agents, Electroanalysis 1999, 11 No. 12, pp. 866-869.

Volotovsky, V. & Namsoo K., Cyanide Determination by an ISFET-Based Peroxidase Biosensor, Biosensors & Bioelectronics 13 (1998) 1029-1033.

Amine, A. et al., Cyanide Determination Using an Amperometric Biosensor Based on Cytochrome Oxidase Inhibition, Anal. Chem. 1995, 67, 2822-2827.

Lee, S. & Lee W., Determination of Heavy Metal Ions Using Conductometric Biosensor Based on Sol-Gel Immobilized Urease, Bull. Korean Chem. Soc. 2002, vol. 23, No. 8, 1169-1172.

Wang, J. et al., Organic-Phase Biosensing of Enzyme Inhibitors, Analytica Chimica Acta, 279 (1993) 203-208.

Lakard, B., et al., Urea Potentiometric Biosensor Based on Modified Electrodes With Urease Immobilized on Polyethylenimine Films Biosensors & Bioelectronics 19 (2004) 1641-1647.

Rajesh, et al., An Amperometric Urea Biosensor Based on Covalent Immobilization of Urease Onto an Electrochemically Prepared Copolymer Poly (N-3 Aminopropyl Pyrrole-Co-Pyrrole) Film, Biomaterials 26 (2005) 3683-3690.

Badugu, R., et al., A Glucose Sensing Contact Lens: A Non-Invasive Technique for Continuous Physiological Glucose Monitoring, Journal of Fluorescence, vol. 13, No. 5, Sep. 2003, 371-374.

Shih, Y. & Huang H., A Creatinine Deiminase Modified Polyaniline Electrode for Creatinine Analysis, Analytica Chimica Acta 392 (1999) 143-150.

Berberich, J. et al., A Stable Three-Enzyme Creatinine Biosensor. 3. Immobilization of Creatinine Amidohydrolase and Sensor Development, Acta Biomaterialia 1 (2005) 193-199.

* cited by examiner

ENZYME CONTAINING LIQUID AND DELIVERY SYSTEM FOR DETECTION OF ANALYTES ON SURFACES

GOVERNMENT INTEREST

Certain embodiments of this invention were made with Government support under Contract No. W911NF-05-C-0004 awarded by the Defense Threat Reduction Agency (DTRA). The Government has certain rights in the invention.

FIELD OF THE INVENTION

This invention relates to an aqueous enzyme based sensor comprising at least one or more enzymes and at least one indicator compound that indicates reaction of one of the enzymes with a target analyte via either visible color change or machine-readable changes such as, for example, including change in the pH or oxidation state. A dispensing system for delivering the aqueous enzyme based sensor to a surface and a method of detecting the presence of a target analyte on a surface is provided.

BACKGROUND OF THE INVENTION

It is highly desirable to develop a simple product/technology which would enable detection of target chemicals spread over large areas. However, presently used technologies and devices have limitations in effectively achieving this objective. Enzyme-based biosensors are most suitable for detection of toxins such as, for example, but not limited to, pesticides, acids, chemical warfare agents, and toxic industrial chemicals because enzymes can be selectively inhibited by a particular class of chemicals. Enzyme-based biosensors are also used in detecting target chemicals that act as substrates for enzymes. In most biosensors, the sensing enzymes are incorporated in devices such as electrodes, transducers, fiber optics, hydrogels, polymer sponges or crystals, and the target chemical must be physically contacted with the device so as to enable its interaction with the sensing enzyme. This form of operation requires sampling of surfaces and this is not practical over large areas or objects such as public places, buildings, offices, vehicles etc. It is therefore the objective of the present invention to provide enzyme containing liquids that can be sprayed on various surfaces that are suspected to be contaminated with target chemicals and then detect the presence of specific chemical via enzymatic reaction that enables visible or machine-readable signal.

As described above, many biosensors employ the principle of enzyme inhibition by certain class of chemicals. For example, organophosphates inhibit cholinestarases, cyanides inhibit peroxidases, and heavy metals inhibit ureases and so on. These phenomena cause drastic changes in the chemical and/or physical state of the system and these changes are sensed by the read-out mechanism employed in various biosensors.

Similarly, many enzyme-based sensors detect the target analyte by utilizing the analyte itself as a substrate e.g. glucose, urea, creatinine etc. This phenomenon also causes physical/chemical changes in the sensory system of the biosensor used and enables detection of the target analyte. In the following sections we briefly review traditional enzyme based biosensors for a variety of target analytes, which are based either on enzyme inhibition or on enzyme catalysis.

Acetyl cholinesterase based organophosphate sensors: Depending on the potency, phosphoesters of organic alcohols are used either as insecticides, pesticides or as nerve agents in chemical warfare. In both the applications, enzyme acetyl cholinesterase (AChE) in exposed organisms is irreversibly inhibited due to phosphorylation of serine hydroxyl group in the active site of the enzyme. Detection of trace amounts of organophosphates in agriculture and in civilian and military environment is an important area of research. Numerous amperometric and potentiometric sensors comprising AChE have been reported so far (N. Jaffrezic-Renault, Sensors 1, 60-74 (2001)). In these sensors AChE is immobilized on the surface of transducers through different techniques. In amperometric sensors the current generated by oxidation of thiocholine (which is generated by enzymatic hydrolysis of substrate butyrylthiocholine) is measured. Also, a bi-enzymatic system of AChE and choline oxidase has been used to detect organophosphates, wherein, hydrogen peroxide generated by oxidation of choline (which is generated by AChE catalyzed hydrolysis of acetylcholine) is detected. In case of potentiometric sensors such as ion selective electrodes (ISE) or ion sensitive field effect transistor (ISFET), organophosphates are detected by monitoring the change in the pH due to the acid generated from enzymatic hydrolysis of acetylcholine.

Recently, a photonic crystal-AChE based sensor for organophosphates has been reported. This sensor uses AChE immobilized in a polymerized crystalline colloidal array. When trace amounts of organophosphates inhibit AChE, the polymer swells and changes the lattice spacing in crystals causing red-shift in the wavelength of diffracted light (J. P. Walker, S. A. Asher, Anal. Chem. 77, 1596-1600 (2005)).

U.S. Pat. No. 7,008,524 describes the sensor and the method to detect chemical agents using metal interdigitized electrodes coated with polymer film containing AChE. When organophosphates react with AChE in the sensor, chemical and/or morphological changes occur in the polymer film and this modulates the electric current flowing through the electrode. U.S. Pat. No. 6,821,738 describes optical sensor based on reversible complex of AChE and porphyrins or phthalocyanines. When organophosphates react with AChE, they displace the fluorescent porphyrins from the active site of AChE. This causes changes in the absorption and/or fluorescence spectra of porphyrins that are detectable by spectrophotometers. U.S. Pat. No. 6,541,230 describes polyurethane sponges containing AChE, butyrylcholinesterase, organophosphorous hydrolase, and the indicator useful in "verified decontamination" of chemical warfare agents. U.S. Pat. No. 6,750,033 describes polyurethane polymer containing AChE (which is inhibited by organophosphates) and a second base-producing enzyme urease (which is not inhibited by organophosphates). In the absence of organophosphates, the polymer soaked in substrates solution has neutral pH as both the enzymes in the polymer are producing acid and base at controlled rates. When organophosphates are swiped on to sensor, AChE in the polymer is inhibited and pH of the medium is increased. This is visualized by pH sensitive indicator dye incorporated in the polymer.

Organophosphorous hydrolase based organophosphate sensors: Since AChE is irreversibly inhibited by organophosphates the sensors based on AChE are made for single use application. For reusable applications, researchers have developed sensors using organophosphorous hydrolases (OPH) which catalytically hydrolyze organophosphates as their substrates. Mulchandani et al have reviewed the present state of the art in OPH based biosensors which can be broadly categorized into potentiometric, optical and amperometric sensors (A. Mulchandani, W. Chen, P. Mulchandani, J. Wang, K. R. Rogers, Biosensors and Bioelectronics 16, 225-230 (2001)). Potentiometric sensor for organophosphates has been reported by immobilizing a layer of OPH crosslinked with bovine serum albumin and glutaraldehyde on to a pH electrode. The electrode measures change in the pH when it is in contact with the solution containing organophosphates (P. Mulchandani, A. Mulchandani, I. Kaneva, W. Chen, Biosensors and Bioelectronics 14, 77-85 (1999)).

Two different optical sensors containing OPH have been developed. In the first sensor, fluorescein isothiocyanate (FITC) labeled OPH was adsorbed on poly(methyl methacrylate) beads and the sensor beads were contacted with the analyte in a microbead fluorescence analyzer. The presence of organophosphates was detected by monitoring decrease in the fluorescence of FITC label on inhibited AChE. In the second optical sensor, a fiber optic set up was built with desired cut off wavelength of 348 or 400 nm to detect hydrolysis products of organophosphates such as coumaphos or p-nitrophenol, respectively. OPH was immobilized on a nylon membrane and attached to the optical fiber in the set up (A. Mulchandani, S. Pan, W. Chen, Biotechnol. Prog. 15, 130-134 (1999)).

OPH based amperometric sensor for organophosphates has been developed in the form of a screen-printed thick film carbon electrode. The electrode was coated with Nafion membrane containing OPH. p-nitrophenolate anion released by enzymatic hydrolysis of certain organophosphates was oxidized at the anode and the generated current was measured using a potentiostat (A. Mulchandani, P. Mulchandani, W. Chen, J. Wang, L. Chen, Anal. Chem. 71, 2246-2249 (1999)). In a modification of this technique, a remote OPH-based amperometric biosensor was also developed (J. Wang, L. Chen, A. Mulchandani, P. Mulchandani, W. Chen, Electroanalysis 11, 866-869 (1999)).

All these sensors have exhibited very low detection limits ranging between 0.5 to 50 μM concentrations of organophosphates. However, the operating mechanism of these sensors requires that each time the sample must be applied to the electrode or polymer in order to detect the presence of organophosphates. Thus, none of these sensors are particularly conducive for detecting organophosphates spread over open and wide surfaces. Biosensors comprising enzyme-electrodes and based on enzyme-inhibition have been also developed for drugs, cyanide, heavy metals, and chemicals. We briefly review some of these in the following sections.

Peroxidase based cyanide sensors: Horseradish peroxidase (HRP) is reversibly inhibited by cyanide ions. Therefore, HRP based biosensors have been constructed by many researchers to monitor the cyanide traces in water. For example, HRP immobilization on surface of ISFET has been reported (V. Volotovsky, N. Kim, Biosensors and Bioelectronics 13, 1029-1033 (1998). The sensor was constructed by coating the electrode with HRP immobilized in poly(4-vinyl pyridine-co-styrene). The sensor was able to detect 0.6 μM potassium cyanide and was able to be reused after washing. Similarly, HRP based amperometric sensor has been reported by immobilizing the enzyme and an osmium redox polymer ([Os(bipyridyl)$_2$(poly(vinyl pyridine)$_{10}$Cl] Cl) on to an electrode. Upon addition of substrate hydrogen peroxide, a biocatalytic reduction generated the current. This current was inhibited by the analyte cyanide to cause change from 150 mV to 0 mV. Cyanide detection ranged between 4 μM to 40 μM (T-M. Park, E. I. Iwuoha, M. R. Smyth, Electroanalysis 9, 1120-1123 (1997)). A cyanide sensor electrode based on cytochrome oxidase has been also reported (A. Amine, M. Alafendy, J-M. Kauffmann, M. N. Pekli, Anal. Chem. 67, 2822-2827 (1995)). Here also, these sensors are limited to detect cyanide in aqueous samples and are not conducive to determine the presence of cyanide on surfaces.

Urease based heavy metal ion sensors: Urease is inhibited by toxic heavy metal ions such as mercury, lead, and cadmium. Thus, urease based sensors have been constructed to detect trace amounts of heavy metal ions in drinking water and industrial effluents. For example, a conductometric urease biosensor has been reported for detection of $Hg^{+2}$, $Cu^{+2}$, $Cd^{+2}$, and $Pb^{+2}$ ions (S-M. Lee, W-Y. Lee, Bull. Korean Chem. Soc. 23, 1169-1172 (2002)). The sensor was constructed by immobilizing the enzyme-silica sol-gel as a thick film on screen printed interdigitated array electrode. Inhibition of urease by heavy metal ions was measured from the difference in the admittance response for 1 mM urea before and after the interaction with metal ions. Also, urease based optical biosensor for heavy metals have been constructed by immobilizing the enzyme on aminopropyl glass. Heavy metals were detected by monitoring changes in pH resulting from urease catalyzed hydrolysis of urea before and after the incubation with metal ions (R. T. Andres, R. Narayanaswamy, The Analyst, 120, 1549-1554 (1995)).

Enzyme based toxic chemical sensors: Amperometric sensors for detection of thiols, carbamates, thiourea, and benzoic acid have been reported by using tyrosinase and peroxidase electrodes (J. Wang, E. Dempsey, A. Eremenko, Anal. Chim. Acta 279, 203-208 (1993)). Aqueous solutions of enzyme and crosslinking polymer were applied to an electrode to form the enzyme-containing film layer around the electrode. Detection of chemicals was performed by measuring the current generated upon addition of 0.2 mM phenol before and after the incubation with the chemical.

Enzyme based sensors for analytes used as substrates: Urease catalytically hydrolyzes urea into ammonia, carbon dioxide and water. Urea can be present as adulterant in milk. Also, urea can be present in river water and in industrial effluents. Therefore, urease based biosensors have been developed to detect urea in various aqueous samples. For example, potentiometric urea sensor has been developed by coating the surface of a microelectrode with crosslinking mixture of urease, polyethyleneimine, and glutaraldehyde. The sensor exhibited short response time (15-30 seconds) and linear detection range of 1-100 mM urea (Lakard, B., Herlem, G., Lakard, S., Antoniou, A., Fahys, B., Biosensors and Bioelectronics 19, 1641-1647 (2004)).

Similarly, amperometric urea biosensor has been developed by immobilizing urease-containing conducting polymer film of poly((N-3-aminopropyl pyrrole-co-pyrrole) onto an electrode (Bisht, R. V., Takashima, W., Kaneto, K., Biomaterials 26, 3683-3690 (2005)). The electrode measured the redox current generated by pH sensitive redox compound hematein. The electrode gave linear response in the range of 0.16-5.0 mM urea in aqueous medium.

For diabetic population, glucose is an important analyte detected by glucose oxidase based biosensors that oxidize the substrate glucose into gluconic acid. A variety of blood glucose sensors are available in the market that are based on glucose oxidase. Apart from this, there is continuously ongoing research in the field of glucose sensors to improve sensor operations and patient comfort levels. For example, glucose sensing contact lens has been reported to monitor glucose levels in tears (Badugu, R., Lakowicz, J. R., Geddes, C. D. Journal of Fluorescence 13, 371-373 (2003)). The contact lens uses boronic acid containing flourophore which reacts with vicinal diols in glucose and changes its fluorescence to detect 0.05-1.0 mM glucose in tears, which can be tracked to 5-10 fold higher glucose level in the blood.

Creatinine is yet another important health-biomarker which can be detected using enzyme based sensors. For example, potentiometric biosensor for creatinine has been reported by using electrode modified with creatinine deiminase, the enzyme that degrades creatinine to produce ammonia (Shih, Y., Huang, H., Anal. Chim. Acta 292, 143-150 (1999)). Interestingly, creatinine amidohydrolase, the enzyme that converts creatinine into creatine has been also used to develop an amperometric biosensor (Berberich, J. A., Chan, A., Boden, M., Russell, A. J., Acta Biomaterialia 1, 193-199 (2005).

All of the background art mentioned above for enzyme based sensors can detect the analyte of interest when it is present in the sample solution applied to the sensor. But none of these background art sensors have the ability to detect the analyte present on a surface without sampling the surface. Sensing analytes on surfaces is an important capability useful in security applications such as detection of nerve agents and toxic chemicals spread over the area in question. It is therefore the objective of the present invention to provide aqueous enzyme containing liquids that are applied to a surface for detection of target analytes.

SUMMARY OF THE INVENTION

The present invention provides an aqueous enzyme based sensor comprising a single or multiple enzymes, and at least one indicator compound that indicates reaction of at least one of the enzymes with at least one target analyte wherein the enzyme and the indicator are capable of being delivered to a surface having the target analyte. Preferably the liquid containing the enzyme based sensor is sprayed onto the surface in order to detect the presence of a target chemical. The aqueous based sensor of this invention is capable of detecting an enzyme specific substrate as the analyte. In another embodiment of the present invention, the aqueous enzyme based sensor comprises one or more enzyme specific substrates in which the enzyme based sensor detects enzyme inhibition. This aqueous enzyme based sensor provides wherein the indicator compound senses at least one of a visible color change or machine-readable changes in the system including change in the pH, oxidation state or substrate concentration.

The aqueous enzyme based sensor of the present invention provides that each of the enzyme, indicator compound and the enzyme specific substrate is either a liquid or a solid that is capable of being dissolved in water. Preferably, the solid is a lyophilized powder that is reconstituted with a sufficient amount of water to a desired concentration. A sufficient amount of water is that amount of water required to reconstitute a solid or powder material into a liquid form and to achieve a liquid having a desired concentration.

It is therefore the objective of the present invention to describe a process for the preparation of sprayable enzyme containing liquids that are useful in detecting analytes on surfaces via enzymatic action on the analyte without requiring sampling of the surface.

It is a further objective of the invention to describe a process for the preparation of solid powders which can be stored for extended periods of time and at a later time dissolved preferably with water to reconstitute the solid powders thus allowing for the regeneration of the enzyme containing liquids when required.

In another embodiment of this invention, a dispensing system is provided for delivering an aqueous enzyme based sensor to a surface comprising an aqueous based sensor as described in this invention herein, and a liquid dispensing device for delivering the aqueous enzyme based sensor to the surface. Preferably the dispensing system comprises a liquid dispensing device that is capable of spraying the aqueous enzyme based sensor onto the surface having a target chemical. The dispensing system of the present invention allows for the detection of a target analyte without the need for sampling of the surface.

In yet another embodiment of this invention, the dispensing device as described herein provides a multi-chambered system for storing, mixing and delivering to a surface at least the enzyme, and indicator compound, and optionally the enzyme specific substrate. Preferably, the aqueous enzyme based sensor of this invention is sprayed on to the surface for the detection of a target chemical.

A method of detecting the presence of a target analyte on a surface is provided comprising spraying a surface with the aqueous enzyme based sensor of this invention, and detecting the presence of a target analyte by observing a visible color change or a machine readable change in the pH or oxidation state. No sampling of the surface is required in the present method.

DETAILED DESCRIPTION OF THE INVENTION

One embodiment of this invention is to provide a readily dispensable aqueous delivery vehicle that can be used to deliver enzyme chemistry to a surface in order to identify the presence of a target chemical. Accordingly, the present invention provides spray-able liquid comprising an enzyme which reacts with the target analyte, an optional second enzyme which does not react with the target analyte, substrates for both the enzymes, an indicator to indicate the reaction of the first enzyme with the target analyte, and optionally a light scattering additive, an adhesive polymer, and a surfactant and a solvent to dissolve the water-insoluble target analyte. The enzyme containing liquid can be stored separately as solid enzyme, preferably as a lyophilized powder, and solid indicator compound and the optional solid enzyme specific substrate, light scattering additives, adhesive polymers, protein stabilizers, protein stabilizing sugars, surfactants, solvents and combinations thereof, placed in separate chambers of a commercially available multi-chambered (preferably dual chambered) liquid dispensing device, preferably capable of producing a spray for delivery to a surface. At the time of application, the solid enzyme(s), indicator compound(s), and the optional enzyme specific substrate(s), light scattering additive(s), adhesive polymer(s), protein stabilizer(s), protein stabilizing sugar(s), surfactant(s), solvent(s), and combinations thereof, are reconstituted by adding water to each chamber of the dispensing device, drawing the water reconstituted solids (now liquids) from each chamber into a mixing area of the dispensing device for effecting a mixture of at least one or more enzymes and at least one or more indicator compounds, and optionally one or more enzyme specific substrates, light scattering additives, adhesive polymers, protein stabilizers, protein stabilizer sugars, surfactants, solvents and combinations thereof, and then delivering the mixture of the aqueous enzyme based sensor from the dispensing device to a surface, preferably through a spray head of the dispensing device. Preferably, the reconstitution of the solid materials as set forth herein are effected just prior to the delivery of the mixture of aqueous enzyme based sensor is applied to a surface.

Thus, the present invention provides an aqueous enzyme based sensor comprising one or more enzymes and at least one indicator compound capable of indicating a reaction of at least one of the enzymes with at least one target analyte, wherein the enzyme and the indicator are capable of being delivered to a surface having the target analyte without the need to sample the surface. This aqueous enzyme based sensor of is capable of being sprayed onto the surface in order to detect the presence of a target chemical. The enzyme, for example but not limited to, is selected from a group consisting of cholinesterases, ureases, peroxidases, and proteases, and combinations thereof.

In another embodiment of this invention, the aqueous enzyme based sensor is capable of detecting an enzyme specific substrate as the analyte. In this embodiment, it is preferable that the enzymes are at least one selected from the group consisting of ureases, peroxidases, and proteases, and combinations thereof.

Another embodiment of this invention provides wherein the aqueous enzyme based sensor of this invention comprises of one or more enzyme specific substrates in which the enzyme based sensor detects enzyme inhibition. In this embodiment, it is preferable that the enzymes are at least one selected from the group consisting of cholinesterases, proteases, and peroxidases and combinations thereof. The enzyme specific substrate is, for example but not limited to, at least one selected from the group consisting of acetylcholine, butyrylcholine, urea, N-benzoyl arginyl ethyl ester, hydrogen peroxide, and N-benzoyl arginyl p-nitroanilide for producing acid or base or chromogenic or oxidized product upon enzymatic reaction. The aqueous enzyme based sensor of this invention provides wherein the indicator senses at least one of a visible color change, a change in pH, oxidation state or substrate concentration.

The aqueous enzyme based sensor of this invention as described herein may optionally comprise one or more of a light scattering additive, an adhesive polymer, a protein stabilizer, a protein stabilizing sugar, a surfactant, and a solvent, and combinations thereof.

The indicator compound is a ph indicator dye that is selected from the group consisting of cresol red, phenol red, metacresol purple, neutral red, and curcumin, etc.

Another embodiment of this invention provides wherein the indicator compound may be a pH sensitive fluorescent dye selected from the group consisting of carboxy-seminaphthorhodaflur (carboxy-SNARF) and fluorescein, etc. Yet, another embodiment of this invention provides that the indicator compound may be a chemiluminescent chemical that emits light upon enzymatic reaction selected from the group consisting of luminol and oxatane, etc. In another embodiment of this invention the indicator compound is a redox dye selected from the group consisting of guaiacol, 4-aminoantipyrine, and 3-(N-Ethyl-3-methylanilino)-2-hydroxypropanesulfonic acid (EHSPT), etc.

The aqueous enzyme based sensor of this invention as described herein provides that the light scattering additive is, for example, an insoluble particulate metal oxide. Preferably the metal oxide is a titanium dioxide or a silica-coated titanium dioxide.

The aqueous enzyme based sensor of this invention as described herein provides that the protein stabilizer is selected from the group consisting of poly(ethylene glycol), poly(N-vinyl pyrrolidone), dextran, poly(vinyl alcohol), and poly(ethylene imine), etc.

The aqueous enzyme based sensor of this invention as described herein provides that the adhesive polymer is selected from the group consisting of poly(vinyl alcohol), carboxymethyl cellulose, and hydroxypropylmethyl cellulose, etc.

The aqueous enzyme based sensor of this invention as described herein provides that the protein stabilizing sugar is selected from the group consisting of sucrose, trehalose, mannitol, xylitol, maltose, dextrose, and glucose, etc.

The aqueous enzyme based sensor of the present invention as described herein provides that the surfactant is, for example, selected from the group consisting of polyethylene glycol p-(1,1,3,3-tetramethylbutyl)-phenyl ether (Triton X-100, Dow Chemical Company), polyoxyethylene (20) sorbitan monooleate (Tween-80, ICI Americas, Inc), polyoxyethylene (20) sorbitan monolaureate (Tween-20, ICI Americas, Inc.), polyoxyethylene lauryl ether (Brij-35, Caledon Laboratories Ltd.), lauramine oxide (AO-12, Mason Chemical Company), and sodium di-2-ethyl-hexyl-sulphosuccinate (AOT), etc.

The aqueous enzyme based sensor of this invention as described herein provides that the solvent is selected from the group consisting of xylene, toluene, hexane, heptane, octane, acetone, ethanol, and methanol, etc.

Preferably, the aqueous enzyme based sensor of this invention provides wherein the enzyme is an aqueous liquid, the indicator compound is an aqueous liquid, and optionally, the enzyme specific substrate is an aqueous liquid. In another embodiment of this invention, the enzyme, the indicator compound and the optional enzyme specific substrate are each a solid that is capable of being dissolved in water. The solids are preferably a lyophilized powder. It will be understood by those skilled in the art that a solid is a phase of matter characterized by resistance to deformation and to changes in volume. A powder is a substance that has been crushed into very fine grains. It is preferable that the lyophilized powders of this invention have a particle diameter size ranging from about 50 nanometers to about 1000 nanometers. In a preferred embodiment of this invention, the enzyme specific substrate and the indicator compound are mixed together and then combined with the enzyme. In another embodiment of this invention, the aqueous enzyme based sensor provides wherein the enzyme lyophilized powder is prepared by lyophilizing a single enzyme or multiple enzymes in the presence of at least one stabilizing additive selected from the group consisting of a stabilizing polymer, a sugar, and combinations thereof. In yet another embodiment of this invention, the aqueous enzyme based sensor provides wherein the enzyme lyophilized powder is prepared by lyophilizing multiple enzymes individually and by mixing the individually lyophilized enzyme powders together to obtain the enzyme powder.

In another embodiment of this invention, the aqueous enzyme based sensor provides wherein the enzyme specific substrate powder is prepared by lyophilizing a single or multiple substrates in the presence of at least one stabilizing polymer, at least one sugar, and the indicator compound, and at least one adhesive polymer, and light scattering additive.

A dispensing system for delivering an aqueous enzyme based sensor to a surface is provided comprising an aqueous enzyme based sensor comprising one or more enzymes, and at least one indicator compound capable of indicating a reaction of at least one of the enzymes with at least one target analyte wherein the enzyme and the indicator compound are capable of being delivered to a surface having the analyte; and a liquid dispensing device for delivering the aqueous enzyme based sensor to the surface.

In another embodiment of this invention, the dispensing system as set forth herein provides wherein the aqueous enzyme based sensor is capable of detecting an enzyme specific substrate as the analyte.

Another embodiment of this invention provides the dispensing system as described herein wherein the aqueous enzyme based sensor comprises one or more enzyme specific substrates in which the enzyme based sensor detects enzyme inhibition. The aqueous enzyme based sensor as described herein may further comprises one or more of a light scattering additive, an adhesive polymer, a protein stabilizer, a protein stabilizing sugar, a surfactant, and combinations thereof. Any of the hereinbefore described embodiments of the aqueous enzyme based sensor of this invention may be employed in the dispensing system of this invention.

Figure 1:
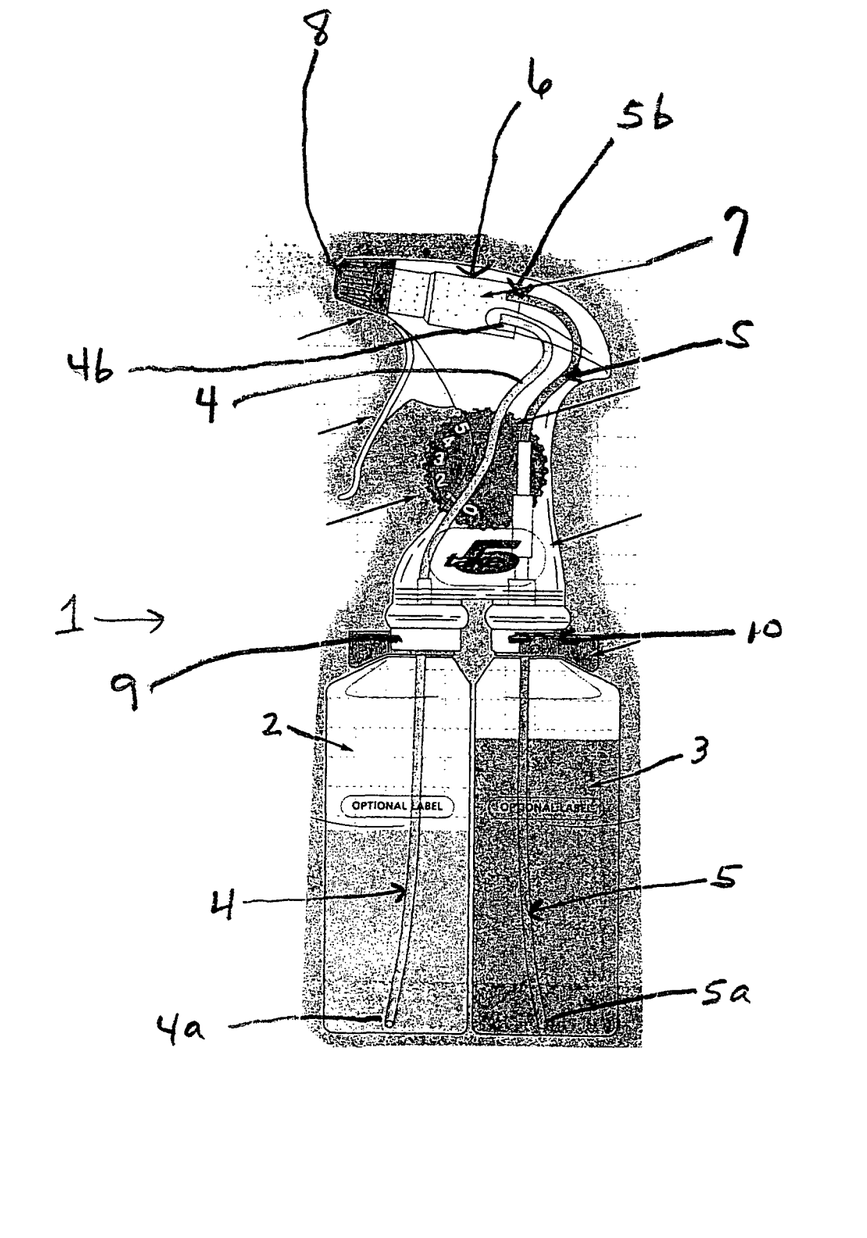
FIG. 1 is a schematic of one example of a dispensing device employed in the dispensing system of this invention.

FIG. 1 shows an embodiment of the present invention wherein the dispensing system as described herein, comprises a liquid dispensing device (1) comprising a first chamber (2) for containing one or more of the enzymes; a second chamber (3) for containing the indicator compound, wherein the first chamber (2) and the second chamber (3) each have a separate conduit (4,5), respectively, each of the conduits (4,5) having one end (4a, 5a), respectively, in communication with a chamber (2, 3), respectively, and a second end (4b, 5b), respectively, in communication with a spray head (6), the conduits (4,5) allowing for the passage of the enzyme, and the indicator compound, respectively, out of the first (2) and second (3) chambers, respectively, and into a mixing area (7) of the spray head (6) such that the enzyme located in the first chamber (2) and the indicator compound located in the second chamber (3) are capable of mixing together in the mixing area (7) of the spray head (6); and a pump device (not shown in FIG. 1) that is in communication with the mixing area (7) of the spray head (6) wherein the pump device is capable of drawing at the same time a desired amount of each of the enzyme from the first chamber (2) and through the first conduit (4) into the mixing area (7) and the indicator compound from the second chamber (3) through the second conduit (5) into the mixing area (7) for accomplishing the mixing of the enzyme and the indicator compound; and a spray nozzle (8) in communication with the mixing area (7) of the spray head (6) for delivering a desired amount of the mixture of the enzyme and the indicator compound from the mixing area (7) to a surface. The dispensing system provides wherein said enzyme located in the first chamber (2) and the indicator compound located in the second chamber (3) are aqueous liquids. Preferably, the dispensing system's spray nozzle (8) is capable of delivering a mist of the mixture of the aqueous enzyme based sensor of this invention onto a surface wherein the mist mixture has a particle diameter size ranging from about 10 to about 1000 nanometers, and preferably from about 10 nanometers to about 500 nanometers. The dispensing system further may provide that the mist delivered from said spray nozzle (8) is capable of adhering to a vertical surface. The dispensing system further comprises wherein the aqueous enzyme based sensor comprises at least one of a light scattering additive, an adhesive polymer, a surfactant, and a solvent, and combinations thereof, all of which is preferably housed in the second chamber (3) separated from the first chamber (2) that is housing the enzyme.

In another embodiment, the dispensing system as described herein comprises wherein the first chamber (2) comprises a first resealable port (9) in communication with a wall of the first chamber (2) for allowing entry and discharge of liquids or matter in and out of the first chamber (2), and wherein the second chamber (3) comprises a second resealable port (10) in communication with a wall of the second chamber (3) for allowing entry and discharge of liquids or matter in and out of the second chamber (3).

In a more preferred embodiment of this invention, the dispensing system as described herein comprises wherein the first chamber (2) contains the enzyme in a solid state that is capable of being dissolved by the addition of water via said first port (9), and wherein the second chamber (3) contains the indicator compound in a solid state that is capable of being dissolved by the addition of water via the second port (10). Most preferably, the solid enzyme and the solid indicator compound are each a lyophilized powder having a particle size ranging from about 10 nanometers to about 1000 nanometers and preferably from about 50 nanometers to about 1000 nanometers. The dispensing system further comprising water reconstituted lyophilized enzyme and water reconstituted lyophilized indicator compound. In another embodiment, the dispensing system as described herein is capable of detecting an enzyme specific substrate as the analyte.

Another embodiment of the dispensing system of this invention as described herein comprises one or more enzyme specific substrates in which the enzyme based sensor detects enzyme inhibition. The dispensing system provides that the enzyme specific substrate is an aqueous liquid or is a solid that is capable of being dissolved in water. Preferably, the solid is a lyophilized powder. The dispensing system preferably comprises water reconstituted lyophilized enzyme specific substrate. Employing this dispensing system, the presence of a target analyte is detected by observing a visible color change or machine readable change in the pH, oxidation state, or substrate concentration.

Another embodiment of this invention provides a method of detecting the presence of a target analyte on a surface comprising spraying a surface with an aqueous enzyme based sensor as described herein; and detecting the presence of a target analyte by observing a visible color change or a machine readable change in the pH, or oxidation state. In another embodiment, this method of this invention provides wherein the aqueous enzyme based sensor is capable of detecting an enzyme specific substrate as the analyte.

In yet another embodiment of this method of this invention, the aqueous enzyme based sensor comprises one or more specific substrates in which the enzyme based sensor is capable of detecting enzyme inhibition.

In another embodiment, the enzyme containing liquid may be stored as lyophilized powder.

In another embodiment, the lyophilized powder may be prepared as separate enzyme powder and substrate powder.

In another embodiment, the enzyme powder may be prepared by lyophilizing single enzyme or multiple enzymes in the presence of stabilizing additives such as protein-stabilizing polymers and sugars and combinations thereof.

In another embodiment, the enzyme powder may be prepared by lyophilizing multiple enzymes individually and by mixing the individually lyophilized powders to obtain the enzyme powder.

As stated hereinbefore, it is preferable that the enzyme and the indicator compound be stored in separate chambers of a dispensing device as described herein. Such multiple chambered dispensing devices are known by those skilled in the art. An example of a dual chambered dispensing device that is commercially available is set forth in U.S. Pat. Nos. 5,152,461 and 5,332,157 which are incorporated by reference in their entireties in the present application.

In another embodiment, of the present invention, a dispensing system is provided wherein the aqueous enzyme based sensor as described herein may be sprayed from the commercially available dual chamber sprayer, such as set forth for example in U.S. Pat. Nos. 5,152,461 and 5, 332, 157, onto a surface contaminated with target analyte that reacts with a particular enzyme in the sensor and a visible color change may be observed.

EXAMPLES

Example 1

Enzyme Containing Liquid for Organophosphates Detection Via Visible Color Change A) Preparation of enzymes powder: A predetermined unit activity ratio of AChE (acetyl cholinesterase) to urease (4:1) is mixed together and dissolved in a sufficient amount of water. Unit activity of urease is defined herein as one unit of urease is the amount of enzyme that will liberate 1 micromole of ammonia from urea at pH 7.0 and at 25 degrees Centigrade (C) under the specific assay conditions. Unit activity of acetyl cholinesterase is defined as one unit of AChE is the amount of enzyme that will hydrolyze 1 micromole of acetylcholine into acetic acid and choline at pH 8.0 and at 37 degrees centigrade under the specific assay conditions. A predetermined w/w ratio of stabilizing sugars and polymers to protein (ranging from 1:1 to 100:1) is added in the solution. The clear solution is slowly cooled to −20° C. and then to −80° C. and lyophilized for 2 days to obtain dry enzyme powders. Alternatively, the enzyme solution can be air dried or vacuum dried to obtain the enzyme powder. Alternatively, AChE and urease can be lyophilized separately in the presence of stabilizing sugars and polymers and individual powder can be mixed together.

B) Preparation of substrates powder: Predetermined molar concentrations of substrates urea (3 mM) and acetylcholine (11 mM) are dissolved in water. Predetermined w/w ratios of cresol red (0.01-0.1% w/v of the total spray-able liquid), mannitol (1-10 times the weight of substrates), titanium dioxide nanopowder (0.1-5% w/v of the total spray-able liquid), and carboxymethyl cellulose (0.1-5% w/v of the total spray-able liquid) are added in the substrate solution and homogenized. The homogenized mixture is cooled to −80° C. and lyophilized for 2 days.

C) Spraying enzyme containing liquid from dual chamber sprayer: Predetermined amounts of dried enzyme powder (1-10 mg/mL) and substrate powder (10-100 mg/ml) are added in each chamber of a commercially available dual chamber dispensing device (sprayer) with volume capacity ranging from about 50 mL to about 500 mL for each chamber. One such dispensing device useful for application of aqueous enzyme based sensors is shown in FIG. 1. At the time of application, desired amount of water is added equally to both the chambers and the spray head for dual chamber dispensing device is fitted onto the chambers. The solutions in dual chambers are sprayed through the spray nozzle to dispense the aqueous enzyme based sensor for detection of organophosphates.

D) Performance of enzyme containing liquid in detection of organophosphates: A yellow colored aqueous enzyme based sensor of the present invention was sprayed on a surface contaminated with organophosphates (1 mg paraoxon per Petri dish) and it turned a red color within about 5 minutes of its application. This is due to the inhibition of AChE, the acid producing enzyme, and continued activity of urease, the base-producing second enzyme, which drives the pH to basic side where the indicator changes its color from yellow to red. When this same aqueous enzyme based sensor of this invention was sprayed on a clean surface the color of the sprayed liquid remains yellow. The aqueous enzyme based sensor of this invention remains yellow in color in the absence of organophosphates due to a constant pH achieved by equilibrium between the rates of enzymatic reactions that produce acid and base.

Visibility of a droplet of the aqueous enzyme based sensor of this invention (detecting the contamination) is increased on dark surfaces in the presence of light scattering additive, such as for example but not limited to a nanoparticulate titanium dioxide. The sprayed aqueous enzyme based sensor of this invention can adhere to vertical surfaces in the presence of adhesive polymer.

Example 2

Enzyme Containing Liquid for Cyanogen Bromide Detection Via Visible Color Change A) Preparation of enzymes powder: A predetermined unit activity ratio of trypsin to urease (470:1) is mixed together and dissolved in water. A predetermined w/w ratio of stabilizing sugars and polymers to protein (ranging from 1:1 to 100:1) is added in the solution. The clear solution is slowly cooled to −20° C. and then to −80° C. and lyophilized for 2 days to obtain dry enzyme powders. Alternatively, the enzyme solution can be air dried or vacuum dried to obtain the enzyme powder. Alternatively, trypsin and urease can be lyophilized separately in the presence of stabilizing sugars and polymers and individual powder can be mixed together.

B) Preparation of substrates powder: Predetermined molar concentrations of substrates N-benzoyl arginyl ethyl ester (0.3 mM) and urea (0.4 mM) are dissolved in water. Predetermined w/w ratios of metacresol purple (0.01-0.1% w/v of the total spray-able liquid) and titanium dioxide nanopowder (0.1-5% w/v of the total spray-able liquid) are added in the substrate solution and homogenized. The homogenized mixture is cooled to −80° C. and lyophilized for 2 days. The lyophilization process is known by those skilled in the art.

C) Spraying the enzyme containing liquid from dual chamber sprayer: Predetermined amounts of enzyme powder (1-10 mg/mL) and substrate powder (10-100 mg/mL) are added in each chamber of a commercially available dual chamber dispensing device with volume capacity ranging from about 50 mL to about 500 mL for each chamber. One such dispensing device (sprayer) useful for application of aqueous enzyme based sensors of this invention is shown in FIG. 1. At the time of application, desired amount of water is added equally to both the chambers and the spray head for dual chamber sprayer is fitted on to the chambers. The solutions in dual chambers are sprayed through the nozzle to dispense the enzyme containing liquid for detection of organophosphates.

D) Performance of enzyme containing liquid in detection of cyanogen bromide: When purple colored aqueous enzyme based sensor of the present invention was sprayed on a clean surface the color remained purple. This is due to a constant pH achieved by the rates of enzymatic reactions that produce acid and base are in equilibrium. But when the purple colored aqueous enzyme based sensor of this invention is sprayed on a surface contaminated with cyanogen bromide (a blood agent) the color of the sprayed liquid turned yellow within about 5 minutes because urease, the base producing enzyme is inhibited. The second enzyme trypsin, the acid producing enzyme, is still active and drove the pH to acidic side where the indicator changed its color from purple to yellow.

Example 3

Enzyme Containing Liquid for Organophosphates Detection Via Light Emission

Horseradish peroxidase (3 units/mL of total spray-able liquid) and luminol (0.6 mg/mL of total spray-able liquid) are added in the AChE and urease based enzyme containing liquid described in example 1 and sprayed on a surface which is in a dark location and is contaminated with paraoxon (1 mg/mL). After about 5 minutes, hydrogen peroxide (3% w/v) is sprayed on the same surface. Blue light emitted due to the enzymatic oxidation of luminol at basic pH is observed.

Example 4

Enzyme Containing Liquid for Organophosphates Detection Via Fluorescence Measurement Carboxy-SNARF (1.0 mg/mL) is added in AChE and urease based enzyme containing liquid described in example 1. Then dichlorvos, an organophosphate pesticide, is added in enzyme containing liquid at 0.2 mg/mL concentration. Fluorescence emission spectra of the liquid are recorded at 1 minute intervals for 8 minutes. More specifically, 10 mL enzyme based sensor of the present invention comprising urease-urea, AChE-acetylcholine, and a pH sensitive fluorescent indicator (carboxy-seminaphthorhodafluor) was mixed with 2 mg dichlorvos (a commercially available pesticide). The mixture was stirred at 25 degrees C. and its emission spectra was monitored as a function of time. At time (t) equal to zero (0) minutes the emission wavelength of the fluorescent indicator was 600 nanometers (nm), at time equal to 8 minutes the emission wavelength of the fluorescent indicator shifted to 650 nm due to inhibition of AChE by dichlorvos and increase in the pH of the mixture.

Example 5

Enzyme Containing Liquid for Hydrogen Cyanide Detection

A) Preparation of enzymes liquid: Soybean peroxidase (0.06 units/mL) and β-galactosidase (0.3 units/mL) are dissolved in ACES buffer at pH 7.2.

B) Preparation of substrates liquid: 0.5 mL aqueous guaiacol soln. (2% v/v), 0.5 mL aqueous soln. of p-nitrophenyl galacto pyranoside (2 mg/mL) and 7 ascorbic acid (2% w/w) are mixed together.

C) Detection of hydrogen cyanide: Enzyme and substrate solutions are sprayed from a dual chamber sprayer into vials containing aqueous solution that are contaminated or not-contaminated with hydrogen cyanide (1 mg/mL). In the non-contaminated solution, both the enzymes are active and hence, soybean peroxidase oxidizes guaiacol into an intense brown colored material and β-galactosidase hydrolyzes its substrate to release yellow colored p-nitrophenol. The yellow color is masked by the brown color and the liquid appears brown. Thus, if the sample solution is clean the enzyme containing liquid turns from colorless to brown within about 3 minutes. If the sample solution is contaminated, hydrogen cyanide inhibits soybean peroxidase and the brown colored material is not produced. However, β-galactosidase is still active and it produces yellow colored p-nitrophenol. Thus, if the sample solution is clean, the enzyme containing liquid turn from colorless to yellow within about 3 minutes.

Example 6

Enzyme Containing Liquid for Urea Detection

A) Preparation of enzyme powder: A predetermined amount of urease (10-100 unit/mL) is dissolved in water. A predetermined w/w ratio of stabilizing sugars and polymers to protein (ranging from 1:1 to 100:1) is added in the solution. The clear solution is slowly cooled to −20° C. and then to −80° C. and lyophilized for 2 days to obtain dry enzyme powders. Alternatively, the enzyme solution can be air dried or vacuum dried to obtain the enzyme powder.

B) Preparation of indicator powder: Predetermined w/w ratios of cresol red (0.01-0.1% w/v of the total spray-able liquid), carboxymethyl cellulose (0.1-5% w/v of the total spray-able liquid), and titanium dioxide nanopowder (0.1-5% w/v of the total spray-able liquid) are added in water and homogenized. The homogenized mixture is cooled to −80° C. and lyophilized for 2 days.

C) Spraying the enzyme containing liquid from dual chamber sprayer: Predetermined amounts of enzyme powder (1-10 mg/mL) and indicator powder (10-100 mg/mL) are added in each chamber of a commercially available dual chamber dispensing device (sprayer) with volume capacity ranging from about 50 mL to about 500 mL for each chamber. One such dispensing device useful for application of aqueous enzyme based sensors of the present invention is shown in FIG. 1. At the time of application, desired amount of water is added equally to both the chambers and the spray head for dual chamber dispensing device is fitted on to the chambers. The solutions in the dual chambers are sprayed through the spray nozzle of the dispensing device to dispense the aqueous enzyme based sensor of this invention for detection of urea.

D) Performance of enzyme containing liquid in detection of organophosphates: When a yellow colored aqueous enzyme based sensor of this invention is sprayed on a surface contaminated with urea (1 mL of 100 mM urea per tile) it turns a red color within about 5 minutes. This is due to the catalytic hydrolysis of urea to produce ammonia which drives the pH to basic side where the indicator changes its color from yellow to red. When this aqueous enzyme based sensor is sprayed on a clean surface the color of the sprayed liquid remains a yellow color. Since urea, the substrate for the sensing enzyme urease is not present on the surface, there is no change in the pH and, therefore, the color of the sprayed liquid remains yellow (unchanged).

Whereas particular embodiments of the instant invention have been described for the purposes of illustration, it will be evident to those persons skilled in the art that numerous variations and details of the instant invention may be made without departing from the instant invention as defined in the appended claims.

What is claimed is:

1. An aqueous enzyme based sensor comprising:
a mixture of moving liquid suspended in air comprising a composition of
two liquid mobilized enzymes that are acetyl cholinesterase and urease;
one or more cellulose adhesive polymers;
a solvent that is water;
two enzyme substrates that are acetylcholine and urea;
one or more light scattering additives; wherein said compostion has a constant acidic pH below 7.0 when the enzymes are uninhibited;
and optionally at least one additive comprising one or more of a protein stabilizer, a protein stabilizing sugar, and a surfactant, and combinations thereof; and
at least one indicator compound indicating an observable or machine readable reaction that occurs on a surface of an environment, and wherein said liquid enzyme(s), said adhesive polymer(s), said solvent, said light scattering additive(s) and said indicator compound(s) form a[n] sprayable aqueous enzyme based sensor mixture contained in a liquid dispensing device delivered to said surface by a spray nozzle in communication with said liquid dispensing device wherein said spray nozzle suspends the composition in air such that said aqueous enzyme based sensor mixture detects the presence or absence of at least one target analyte on said surface via an in situ reaction on said surface of an environment without the need for sampling of said surface and analyzing the sample elsewhere.

2. The aqueous enzyme based sensor of claim 1 wherein said indicator is a ph indicator dye that is selected from the group consisting of cresol red, phenol red, metacresol purple, neutral red, and curcumin.

3. The aqueous enzyme based sensor of claim 1 wherein said indicator is a pH sensitive fluorescent dye selected from the group consisting of carboxy-seminaphthorhodaflur and fluorescein.

4. The aqueous enzyme based sensor of claim 1 wherein said indicator is a chemiluminescent chemical that emits light upon enzymatic reaction selected from the group consisting of luminol and oxatane.

5. The aqueous enzyme based sensor of claim 1 wherein said indicator is a redox dye selected from the group consisting of guaiacol, 4-aminoantipyrine, and 3-(N-Ethyl-3-methylanilino)-2-hydroxypropanesulfonic acid.

6. The aqueous enzyme based sensor of claim 1 wherein said light scattering additive is an insoluble particulate metal oxide.

7. The aqueous enzyme based sensor of claim 6 wherein said metal oxide is a titanium dioxide or a silica-coated titanium dioxide.

8. The aqueous enzyme based sensor of claim 1 wherein said protein stabilizer is selected from the group consisting of poly(ethylene glycol), poly(N-vinyl pyrrolidone), dextran, poly(vinyl alcohol), and poly(ethylene imine).

9. The aqueous enzyme based sensor of claim 1 wherein said cellulose adhesive polymer is selected from the group consisting of carboxymethyl cellulose, and hydroxypropylmethyl cellulose.

10. The aqueous enzyme based sensor of claim 1 wherein said protein stabilizing sugar is selected from the group consisting of sucrose, trehalose, mannitol, xylitol, maltose, dextrose, and glucose.

11. The aqueous enzyme based sensor of claim 1 wherein said surfactant is selected from a group consisting of polyethylene glycol p-(1,1,3,3-tetramethylbutyl)-phenyl ether, polyoxyethylene (20) sorbitan monooleate, polyoxyethylene (20) sorbitan monolaureate, polyoxyethylene lauryl ether, lauramine oxide, and sodium di-2-ethyl-hexyl-sulphosuccinate.

12. The aqueous enzyme based sensor of claim 1 wherein said indicator senses at least one of a visible color change, a change in pH, oxidation state or substrate concentration.

13. The aqueous enzyme based sensor of claim 1 wherein said enzyme is an aqueous liquid.

14. The aqueous enzyme based sensor of claim 1 wherein said enzyme is a solid that is capable of being dissolved in water.

15. The aqueous enzyme based sensor of claim 1 wherein said indicator compound is an aqueous liquid.

16. The aqueous enzyme based sensor of claim 1 wherein said indicator compound is a solid that is capable of being dissolved in water.

17. The aqueous enzyme based sensor of claim 14 wherein said solid enzyme is a lyophilized powder.

18. The aqueous enzyme based sensor of claim 16 wherein said solid indicator compound is a lyophilized powder.

19. The aqueous enzyme based sensor of claim 17 wherein said enzyme lyophilized powder is prepared by lyophilizing a single enzyme or multiple enzymes in the presence of at least one stabilizing additive selected from the group consisting of a stabilizing polymer, a sugar, and combinations thereof.

20. The aqueous enzyme based sensor of claim 17 wherein said enzyme lyophilized powder is prepared by lyophilizing multiple enzymes individually and by mixing the individually lyophilized enzyme powders together to obtain the enzyme powder.

* * * * *

UNITED STATES PATENT AND TRADEMARK OFFICE
CERTIFICATE OF CORRECTION

| | |
|---|---|
| PATENT NO. | : 9,556,471 B2 |
| APPLICATION NO. | : 11/501296 |
| DATED | : January 31, 2017 |
| INVENTOR(S) | : Keith E. LeJuene et al. |

It is certified that error appears in the above-identified patent and that said Letters Patent is hereby corrected as shown below:

(56) References Cited - Replace "Wang, J. et al., Remote Blosensor for In-Situ Monitoring of Organophosphate Nerve Agents, Electroanalysis 1999, 11 No. 12, pp. 866-869." with --Wang, J. et al., Remote Biosensor for In-Situ Monitoring of Organophosphate Nerve Agents, Electroanalysis 1999, 11 No. 12, pp. 866-899.--

Column 7, Line 15 - Replace "sensor of is capable" with --sensor is capable--

Column 13, Line 64 - Replace "7 ascorbic acid" with --7 µL ascorbic acid--

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*